US006645480B2

(12) United States Patent
Giles

(10) Patent No.: US 6,645,480 B2
(45) Date of Patent: *Nov. 11, 2003

(54) HAIR TREATMENT COMPOSITION

(75) Inventor: Colin Christopher Giles, Bebington (GB)

(73) Assignee: Unilever Home & Personal Care USA, a division of Conopco, Inc., Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/737,651

(22) Filed: Dec. 15, 2000

(65) Prior Publication Data
US 2001/0004632 A1 Jun. 21, 2001

(30) Foreign Application Priority Data
Dec. 17, 1999 (GB) .............................. 9929972

(51) Int. Cl.$^7$ ................................. A61K 7/09
(52) U.S. Cl. ............... 424/70.2; 424/70.1; 424/70; 510/122; 510/47
(58) Field of Search ............ 424/70, 70.1, 47, 424/70.2; 510/124, 122

(56) References Cited

U.S. PATENT DOCUMENTS

| | | | |
|---|---|---|---|
| 3,974,076 A | 8/1976 | Wiersema et al. | 252/8.8 |
| 4,555,349 A | 11/1985 | Butterworth et al. | 252/8.6 |
| 4,767,547 A | 8/1988 | Straathof et al. | 510/517 |
| 4,919,846 A | 4/1990 | Nakama et al. | 252/542 |
| 5,277,899 A | 1/1994 | McCall et al. | 424/71 |
| 5,399,272 A | 3/1995 | Swartley et al. | 252/8.8 |
| 5,508,454 A | 4/1996 | Brancq et al. | 554/69 |
| 5,614,180 A | 3/1997 | Chung | 424/70.19 |
| 5,747,436 A | 5/1998 | Patel et al. | 510/124 |
| 5,759,527 A | 6/1998 | Patel et al. | 424/70.11 |
| 6,096,697 A * | 8/2000 | Wells et al. | 510/127 |
| 6,218,346 B1 * | 4/2001 | Sajic et al. | 510/124 |
| 6,221,817 B1 * | 4/2001 | Guskey et al. | 510/122 |

FOREIGN PATENT DOCUMENTS

| | | |
|---|---|---|
| EP | 0951898 | 10/1999 |
| GB | 2315769 | 2/1998 |
| WO | 94/04125 | 3/1994 |
| WO | 00/07550 | 2/2000 |
| WO | 00/10524 | 3/2000 |

* cited by examiner

Primary Examiner—Yogendra N. Gupta
Assistant Examiner—Elsa Elhilo
(74) Attorney, Agent, or Firm—Milton L. Honig

(57) ABSTRACT

Hair conditioning formulations containing a particular combination of cationic surfactants, have improved hair care benefits while maintaining excellent in-use characteristics. The compositions contain a first cationic surfactant such as cetyl trimethyl ammonium chloride, stearyl trimethyl ammonium chloride and behenyl trimethyl ammonium chloride. A second hydrophilically substituted cationic surfactant such as cocamidopropyl-N-2-hydroxyethylcarbamoylmethyldimethylammonium chloride, and a lipid material such as cetyl alcohol. Although formulations of the invention are based principally on cationic surfactant, and generally contain no anionic or amphoteric surfactant, they provide an acceptable level of cleaning and lathering whilst still conveying the wet slippy feel desired by consumers in connection with conventional hair conditioners.

12 Claims, No Drawings

HAIR TREATMENT COMPOSITION

TECHNICAL FIELD

The present invention relates to hair treatment compositions and more particularly to conditioning hair rinses, which have the effect of cleansing and conditioning.

BACKGROUND OF THE INVENTION

One of the principal components in most cleansing products is a surfactant. Surfactants are used to remove dirt and debris and also to impart a foaming characteristic to the cleansing product which gives the consumer a perceived indication that the product is functioning as a cleanser.

When washing the hair with conventional cleansing compositions, the natural oils are removed together with the dirt and unwanted oils. When too much of the natural oil is removed, for example by especially frequent washing, the hair becomes less easy to comb or style, and subject to static build-up causing "flyaway." Furthermore, the use of such hair treatments as permanent waving, dyeing, teasing, and bleaching can adversely affect the physical condition of hair, as can atmospheric conditions, such as sunlight, which may cause photo-catalysed oxidation. These factors may result in hair with poor texture, which is difficult to manage and comb, whether wet or dry.

Hair conditioners have been developed to try to restore the condition of the hair. These compositions are normally applied to hair after shampooing, left on the hair for a period of time and rinsed off. Products which improve the appearance, feel, and manageability of hair have gained increasing acceptance and popularity with consumers.

Accordingly, compositions which "condition" hair generally improve the manageability, appearance and feel of hair, by reducing dry static and increasing the ease of combing both wet and dry hair. Such conditioning products are well known.

Many conditioning products contain long chain quaternary ammonium compounds combined with lipid materials, such as fatty alcohols. While such products have particularly good cosmetic in-use and rheologic characteristics, they may leave the hair greasy or oily, and subject to resoiling with dirt and sebum.

In recent years, there have been attempts to incorporate higher levels of hair conditioning benefit agents into a cleansing surfactant-based product formulation to give the consumer the benefit of having one product with dual functions, for example, a shampoo with conditioner. The object of such "2-in-1" products is to optimise the deposition of the hair conditioning benefit agent onto the hair surface while maintaining both the maximum cleaning and lathering properties of the formulation.

Problems arise when trying to combine a hair conditioning agent into a cleansing surfactant-based formulation, due to the competing functions of ingredients. For example, the use of one or more conditioning agents in a formulation may suppress the foaming characteristic of the surfactant. Also, reaction or complexation of the surfactant and the conditioning agent lowers the amount of surfactant available.

Thus, when a conditioning agent such as a silicone, or a mineral or vegetable oil, is used in a formulation, normally the amount of surfactant in the formulation is increased so that the formulation will provide a level of foaming and cleansing which is acceptable to the consumer. However, increasing the amount of surfactant used in the formulation lowers the amount of conditioning agent deposited onto a surface. Thus, at high levels of cleansing surfactant the beneficial effect of the conditioning agent is lost. Conversely, if the level of surfactant is maintained then the level of conditioning agent must be lowered and, again, the beneficial effect of the conditioning agent is lost.

It has now been discovered that hair conditioning formulations containing a particular combination of cationic surfactants, have improved hair care benefits while maintaining excellent in-use characteristics.

Surprisingly, although formulations of the invention are based principally on cationic surfactant, and generally contain no anionic or amphoteric surfactant, they provide an acceptable level of cleaning and lathering whilst still conveying the wet slippy feel desired by consumers in connection with conventional hair conditioners. Furthermore, formulations of the invention also provide improved styling benefits to the hair.

SUMMARY OF THE INVENTION

The present invention provides a hair treatment composition having cleansing and conditioning properties comprising, in an aqueous medium:

(i) a first cationic surfactant corresponding to the general formula (I):

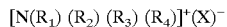

in which $R_1$ is a hydrocarbyl chain having 16 or more carbon atoms, and $R_2$, $R_3$ and $R_4$ are independently selected from hydrocarbyl chains of from 1 to about 30 carbon atoms and X is a salt-forming anion such as those selected from halogen, (e.g. chloride, bromide), acetate, citrate, lactate, glycolate, phosphate nitrate, sulphate, and alkylsulphate radicals;

(ii) a second cationic surfactant corresponding to the general formula (II) or the general formula (III);

general formula (II) being:

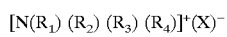

in which $R_1$ is a hydrocarbyl chain having from 8 to 20, preferably from 8 to 18, more preferably from 8 to 14 carbon atoms, and $R_2$, $R_3$ and $R_4$ are independently selected from (a) hydrocarbyl chains of from 1 to about 30 carbon atoms, or (b) functionalised hydrocarbyl chains having from 1 to about 30 carbon atoms and containing one or more aromatic, ether, ester, amido or amino moieties present as substituents or as linkages in the radical chain, X is a salt-forming anion such as those selected from halogen, (e.g. chloride, bromide), acetate, citrate, lactate, glycolate, phosphate nitrate, sulphate, and alkylsulphate radicals, and at least one of the $R_1$ to $R_4$ radicals contains one or more hydrophilic moieties selected from alkoxy (preferably $C_1$–$C_3$ alkoxy), polyoxyalkylene (preferably $C_1$–$C_3$ polyoxyalkylene), alkylamido, hydroxyalkyl, alkylester, and combinations thereof, and, general formula (III) being:

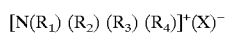

in which $R_1$ is a linear or branched, preferably linear, saturated or unsaturated hydrocarbyl chain having from 5 to 30 carbon atoms, which is linked either directly to the quaternary nitrogen atom or via a functionalised link moiety such as an alkylester, alkylamido or an alkoxy, or combinations thereof;

$R_2$ is a linear or branched, preferably linear, saturated or unsaturated hydrocarbyl chain having from 1 to 30 carbon atoms, and is optionally substituted with one or more hydroxy groups;

$R_3$ is a linear or branched, preferably linear, saturated or unsaturated hydrocarbyl chain having from 1 to 30 carbon atoms, and optionally contains one or more groups selected from hydroxy, alkoxy and polyoxyalkylene groups, and combinations thereof, suitably present as either substituents on the hydrocarbyl chain or as linkages in the hydrocarbyl chain;

$R_4$ is a linear or branched saturated or unsaturated hydrocarbyl chain having from 1 to 30 carbon atoms, and which contains one or more groups selected from hydroxy, aromatic, ether, ester, amido and amino groups, and combinations thereof, suitably present as either substituents on the hydrocarbyl chain or as linkages in the hydrocarbyl chain.

and,

X is a salt-forming anion such as those selected from halogen, (e.g. chloride, bromide), acetate, citrate, lactate, glycolate, phosphate nitrate, sulphate, and alkylsulphate radicals;

(iii) a lipid material having at least one carbon chain of at least 12 carbon atoms in length.

and wherein the first cationic surfactant (i) and second cationic surfactant (ii) together amount to more than 2% by weight of the hair treatment composition.

DETAILED DESCRIPTION OF THE INVENTION

As used herein, the term hydrocarbyl chain means an alkyl or alkenyl chain.

Reference herein in the general formulas (II) to (VI) to the number of carbon atoms in the hydrocarbyl chain means the total number of carbon atoms, including, if present, those in any substituent groups on the hydrocarbyl chain and those in any linkage groups in the hydrocarbyl chain. As will be evident from this definition, a substituent group containing carbon atoms may be viewed as a branching of the hydrocarbyl chain and thus may be referred to as a linkage in the hydrocarbyl chain. This does not effect the calculation of the total number of carbon atoms in the hydrocarbyl chain.

For the avoidance of doubt, the cationic surfactant (ii) only relates to monomeric quaternary ammonium compound, i.e. only contains a sungle quaternary nitrogen atom.

Cationic Surfactant (i)

The hair treatment composition of the present invention comprises, as a first essential component, a cationic surfactant (i) corresponding to the general formula (I) as described above.

Preferred are cationic surfactants containing two long alkyl chains and two short alkyl chains or especially those containing one long alkyl chain and three short alkyl chains. The long alkyl chains in such compounds have 16 or more carbon atoms, preferably from 16 to 22 carbon atoms, and the corresponding short alkyl chains generally have from 1 to 3 carbon atoms, preferably from 1 to 2 carbon atoms.

The most preferred cationic surfactants (i) for compositions of the present invention are those selected from cetyl trimethyl ammonium chloride, stearyl trimethyl ammonium chloride, and behenyl trimethyl ammonium chloride.

Mixtures of any of the foregoing cationic surfactants (i) may also be suitable.

In compositions of the invention, the level of cationic surfactant (i) is preferably from 0.01 to 10%, more preferably 0.1 to 7.5%, most preferably 0.2 to 5% by weight based on total weight of the composition.

Cationic Surfactant (ii)

The hair treatment composition of the present invention comprises, as a second essential component, a cationic surfactant (ii) corresponding to the general formula (II) or general formula (III) as described above.

Preferred subsets of cationic surfactant (ii) of the general formula (III) are those in which:

$R_1$ is a hydrocarbyl chain having from 8 to 20, preferably from 8 to 18, more preferably from 8 to 14 and yet more preferably from 8 to 12 carbon atoms, and, if present, the functionalised link moiety linking the hydrocarbyl chain to the quaternary nitrogen atom is a $C_1$–$C_3$ alkylester, a $C_1$–$C_3$ alkylamido or a $C_1$–$C_3$ alkoxy;

$R_2$ is a hydrocarbyl chain having from 1 to 20, preferably from 1 to 10 carbon atoms and more preferably from 1 to 4 carbon atoms;

$R_3$ is a hydrocarbyl chain having from 1 to 20, preferably from 1 to 10, and more preferably from 1 to 4 carbon atoms, and, if present, any alkoxy or polyoxyalkylene substituent or linkage groups are $C_1$–$C_3$ groups;

$R_4$ is a hydrocarbyl chain having from 1 to 20, preferably from 1 to 10, and more preferably from 1 to 4 carbon atoms, and, if present, any alkoxy or polyoxyalkylene substituent or linkage groups are $C_1$–$C_3$ groups;

In a preferred embodiment, the cationic surfactant (ii) are those corresponding to the general formula (IV):

in which:

R is a linear or branched alkyl or alkenyl radical having from 5 to 30, preferably from 8 to 20, more preferably from 8 to 18 and yet more preferably from 8 to 14 carbon atoms;

m is an integer equal to 2 or 3;

n is an integer equal to 0 or 1;

$R_1$ and $R_2$ are independently:

an alkyl radical having from 1 to 4 carbon atoms, or a hydroxymethyl, hydroxyethyl or hydroxypropyl radical;

p is an integer from 1 to 3;

$R_3$ is a group: $-(CH_2)_q-(O)_y-(CH_2-CH(R_5)-O)_r-H$ in which:

q is an integer from 1 to 5, y is an integer equal to 0 or 1, $R_5$ is a hydrogen atom or a methyl radical, and r is an integer from 0 to 10, it being specified that r and y cannot simultaneously be equal to 0;

or a group: $-(CH_2)_s-(CHOH)_t-(CH_2)_u-CH_3$ in which:

s is an integer from 0 to 2, t is an integer from 0 to 6, and u is an integer from 0 to 5;

or a group: $-(CH_2)_v-(CHOH)_w-CH_2OH$ in which:

v is an integer equal to 0 or 1, and w is an integer from 1 to 6;

$R_4$ is a hydrogen atom or has the same meaning as $R_3$; and

X is a water-soluble salt forming anion, preferably a chloride, bromide or hydroxide ion.

In this definition, the expression "$R_4$ has the same meaning as $R_3$" denotes that $R_4$ can be the same groups as those represented by $R_3$, without $R_3$ and $R_4$ necessarily being identical.

Cationic surfactants (ii) of general formula (IV) and their method of manufacture are described in US 5,508,454

(SEPPIC), and a suitable example is cocamidopropyl-N-2-hydroxyethylcarbamoylmethyldimethylammonium chloride, available commercially as MONTALINEC40 (ex SEPPIC UK).

In another preferred embodiment, the cationic surfactant (ii) have the general formula (V):

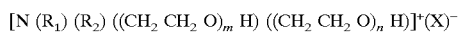

[N (R$_1$) (R$_2$) ((CH$_2$ CH$_2$ O)$_m$ H) ((CH$_2$ CH$_2$ O)$_n$ H)]$^+$(X)$^-$ in which:

R$_1$ is a linear or branched alkyl or alkenyl radical having from 5 to 30, preferably from 8 to 20, more preferably from 8 to 14, yet more preferably from 12 to 14 carbon atoms;

R$_2$ is a C$_1$–C$_3$ alkyl group, preferably methyl, and m and n are each independently integers from 1 to 15, preferably from 1 to 10, more preferably from 1 to 6 and yet more preferably from 1 to 3; and preferably m +n is an integer from 2 to 20, more preferably from 2 to 10 and yet more preferably from 2 to 4;

X is a salt-forming anion such as those selected from halogen, (e.g. chloride, bromide), acetate, citrate, lactate, glycolate, phosphate nitrate, sulphate, and alkylsulphate radicals.

In a preferred subset of general formula (V), at least one of m and n is equal to 1, and preferably both are equal to 1.

Suitable examples of compositions according to general formula (V) are PEG-n alkyl ammonium chlorides (where n is the PEG chain length), such as PEG-2 cocomonium chloride under the trade name of Ethoquad C/12 (ex Akzo Nobel), and PEG-15 cocomonium chloride under the trade name of Berol 556 (ex Akzo Nobel).

In yet another preferred embodiment, the cationic surfactant (ii) have the general formula (VI):

[N(R$_1$) (R$_2$) (R$_3$) (CH$_2$ CH$_2$ O)$_m$ H)]$^+$(X)$^-$ in which:

R$_1$ is a linear or branched alkyl or alkenyl radical having from 5 to 30, preferably from 8 to 20, more preferably from 8 to 14 and yet more preferably from 12 to 14 carbon atoms;

R$_2$ and R$_3$ are independently selected from C$_1$–C$_3$ alkyl groups, and are preferably methyl, and m is an integer from 1 to 15, preferably from 1 to 10, more preferably from 1 to 6, yet more preferably from 1 to 3, and most preferably m is equal to 1;

X is a salt-forming anion such as those selected from halogen, (e.g. chloride, bromide), acetate, citrate, lactate, glycolate, phosphate nitrate, sulphate, and alkylsulphate radicals.

A suitable example is coconutalkyldimethyl (2-hydroxyethyl) ammonium chloride under the trade name of HOE S3996 (ex Clariant).

The total amount of cationic surfactant (ii) in compositions of the invention may suitably range from 1 to 40%, preferably 2 to 30%, most preferably 5 to 15% by weight based on total weight of the composition.

The total amount of cationic surfactant (i) and cationic surfactant (ii) combined in the compositions of the invention is greater than 2% by weight, preferably at least 5% by weight and more preferably at least 10% by weight based onthe total weight of the composition.

The compositions of the invention preferably contain more than 1 wt %, more preferably at least 2 wt % and yet more preferably at least 5 wt % of water-soluble surfactant (s). Preferably, the compositions of the invention contain more than 1 wt %, more preferably at least 2 wt % and yet more preferably at least 5 wt % of water-soluble cationic surfactant (i) and/or cationic surfactant (ii) in the composition. Water-insoluble is taken to mean surfactant materials which do not form clear isotropic solutions when dissolved in water at greater than 0.2 percent by weight at 25° C.

Lipid Material

The hair treatment composition of the present invention comprises, as a third essential component, a lipid material having at least one carbon chain of at least 16 carbon atoms in length.

It is thought that inclusion of such a material enables the cationic surfactant (i) to be present in the composition as a disperse lamellar phase rather than in micellar form as it does in a simple aqueous solution.

Lipid materials are essentially water-insoluble, contain hydrophobic and hydrophilic moeities, and include naturally or synthetically-derived acids, acid derivatives, alcohols, esters, ethers, ketones, and amides with carbon chains of at least 12, preferably at least 14, and more preferably from 16 to 22, carbon atoms in length. Fatty alcohols and fatty esters are preferred; fatty alcohols are particularly preferred.

Preferred fatty esters for use in compositions of the invention include cetyl palmitate and glycerol monostearate. Examples of suitable fatty alcohols are those fatty alcohols having at least 12, preferably at least 16 to 22, carbon atoms, such as lauryl, cetyl, stearyl and behenyl alcohols, and mixtures thereof, which themselves contribute to the overall conditioning properties of the composition.

The total amount of lipid material in compositions of the invention may suitably range from 1 to 30%, preferably 2 to 20%, most preferably 5 to 15 by weight based on total weight of the composition, the amount being sufficient to convert the cationic surfactant (i) to the lamellar liquid crystal phase. The weight ratio of cationic surfactant (i) to lipid material is suitably from 10:1 to 1:10, preferably from 4:1 to 1:8, optimally from 1:1 to 1:7.

Foaming Properties of the Composition

Although compositions according to the invention are typically based primarily on cationic surfactants, their foaming power is excellent compared with conventional rinse-off hair conditioning compositions.

The test-method which can be used to assess the foaming power of compositions according to the invention is the ASTM D 1173-53 test, also referred to as the Ross-Miles test, and described in J Ross and G D Miles, American Society for Testing Materials, 1953, pages 644–646.

Compositions according to the invention generally have a foam height of more than 20 mm, preferably more than 50 mm, more preferably more than 60 mm, and most preferably more than 80 mm, when measured by the foam height test described above.

Product Form

The compositions of the invention may suitably be in the form of a rinse-off conditioner, a leave-on conditioner or a conditioning mousse.

Optional Ingredients

Further surfactants such as anionic or amphoteric surfactants may be added as optional ingredients to compositions of the invention. Preferably, however, the total amount of anionic and/or amphoteric surfactant is no more than 6%, preferably no more than 4.5%, more preferably no more than 3%, by weight based on total weight of the composition.

Compositions according to the invention can optionally include additional conditioning agents for hair such as silicones.

Silicones are particularly preferred conditioning agents for hair. Representative silicones include volatile and non-volatile silicones, such as for example polyalkylsiloxanes (optionally end-capped with one or more hydroxyl groups), polyalkylaryl siloxanes, siloxane gums and resins, cyclomethicones, aminofunctional silicones, quaternary silicones and mixtures thereof.

Preferred silicones include polydimethylsiloxanes (of CTFA designation dimethicone), siloxane gums, aminofunctional silicones (of CTFA designation amodimethicone) and hydroxylated polydimethylsiloxanes (of CTFA designation dimethiconol).

Various methods of making emulsions of particles of silicones are available and are well known and documented in the art.

Suitable silicone emulsions are commercially available in a pre-emulsified form. This is particularly preferred since the pre-formed emulsion can be incorporated into the composition by simple mixing.

Examples of suitable pre-formed emulsions include emulsions DC2-1310, DC2-1865, DC2-1870, DC2-1766 and DC2-1784, available from Dow Corning. These are emulsions of dimethiconol. Siloxane gums are also available in a pre-emulsified form, which is advantageous for ease of formulation. A preferred example is the material available from Dow Corning as DC X2-1787, which is an emulsion of cross-linked dimethiconol gum.

The amount of silicone incorporated into compositions for use according to the invention depends on the level of conditioning desired and the material used. A preferred amount is from 0.01 to about 10% by weight of the total composition although these limits are not absolute. The lower limit is determined by the minimum level to achieve conditioning and the upper limit by the maximum level to avoid making the hair and/or skin unacceptably greasy. We have found that an amount of silicone of from 0.5 to 1.5% by weight of the total composition, is a particularly suitable level.

Compositions of the invention may also optionally include a viscosity enhancer.

Examples of viscosity enhancers include:

cellulose derivatives such as methylcellulose, hydroxymethylcellulose, hydroxyethyl cellulose, hydroxypropylcellulose, and hydroxypropyl methylcellulose;

water-soluble salts of cellulose ethers such as sodium carboxymethyl cellulose and sodium carboxymethyl hydroxyethyl cellulose;

natural gums such as carrageenan, xanthan gum, gum arabic, gum tragacanth and guar gum and derivatives thereof such as hydroxypropyl guar and guar hydroxypropyl trimonium chloride;

inorganic thickeners such as colloidal magnesium aluminium silicate (Veegum), finely divided silica, natural clays such as bentonite and synthetic clays such as the synthetic hectorite available as Laponite (ex Laporte Industries Ltd);

vinyl-type polymeric thickeners such as polyvinylpyrrolidone, polyvinyl alcohol, sodium acrylate/vinyl alcohol copolymers and carboxyvinyl polymers, such as those polymers of acrylic acid crosslinked with about 0.75% to 2.0% of polyallylsucrose or polyallylpentaerythritol, obtainable under the Carbopol trademark from B.F.Goodrich.

As the viscosity enhancer, cellulose derivatives are particularly preferred, especially hydroxyethyl cellulose.

Compositions of the invention in the form of a conditioning mousse will generally contain an aerosol propellant. This agent is responsible for expelling the other materials from the container, and forming the mousse character.

The propellant gas can be any liquifiable gas conventionally used for aerosol containers. Examples of suitable propellants include dimethyl ether, propane, n-butane and isobutane, used singly or admixed. Other examples of suitable propellants include nitrogen, carbon dioxide and compressed air.

The amount of the propellant gases is governed by normal factors well known in the aerosol art. For mousses the level of propellant is generally from about 2 to about 15%, optimally from about 4 to about 10%, by weight based on total weight of the composition.

As further optional components for inclusion in compositions according to the invention may be mentioned the following conventional adjunct materials known for use in cosmetic compositions: emulsifiers, humectants, suspending agents, rheology modifiers, pearlescing agents, opacifiers, salts, perfumes, buffering agents, colouring agents, emollients, moisturisers, foam stabilisers, sunscreen materials, antimicrobial agents, preservatives, antioxidants, and natural oils and extracts.

The invention will now be further illustrated by the following, non-limiting Examples, in which all percentages are by weight based on total weight, unless otherwise stated.

EXAMPLES

Formulations were prepared as follows:

Example 1

| Ingredient | wt % |
| --- | --- |
| Cetyltrimethylammonium chloride | 2.0 |
| Behenyl alcohol | 9.8 |
| Natrosol HHXR, ex Aqualon | 0.8 |
| MONTALINE ® C40, ex Seppic | 10.0 |
| Water, minors | q.s. |

Example 2

| Ingredients | wt % |
| --- | --- |
| Cetyltrimethylammonium chloride | 2.0 |
| Behenyl alcohol | 9.8 |
| Natrosol HHXR, ex Aqualon | 0.5 |
| MONTALINE ® C40, ex Seppic | 10.0 |
| Silicone DC2 1310, ex Dow Corning | 0.5 |
| Water, minors | q.s. |

Comparative Example A—2 in 1 shampoo

| Ingredients | wt % |
| --- | --- |
| Sodium lauryl ether sulphate (SLES) | 14.0 |
| Cocamidopropylbetaine (CAPB) | 2.0 |
| CARBOPOL ® 980, ex BF Goodrich | 0.2 |
| Ethylene glycol distearate (EGDS) | 1.5 |
| Silicone X2 1766, ex Dow Corning | 1.5 |
| Water, minors | q.s. |

Comparative Example B—(i) Shampoo + (ii) Conditioner (applied sequentially)

| Ingredients | wt % |
|---|---|
| (i) Shampoo | |
| SLES | 14 |
| CAPB | 2 |
| EGDS | 1.5 |
| Salt | 0.6 |
| (ii) Conditioner | |
| Cetyltrimethylammonium chloride | 1.0 |
| Cetyl alcohol | 3.0 |
| Water, minors | 0.5 |

TEST METHODOLOGY

The prototypes were applied and assessed by expert hairdressers in half head experiments (36 heads per test). A fixed quantity of each prototype was applied to the hairdresser to each side of the head. The product was then used in accordance with a normal procedure. The hairdresser assessed the panellists hair for a number of attributes and chose which side gave a greater sensation for each attribute or gave no selection. After the treatment was complete the panellist also assessed their finished hair on some of the key attributes.

EVALUATION RESULTS

Voting Splits in a half head salon test are shown in the Table below for the attributes described:

| | Ex 1 vs Comp A | | Ex 1 vs Comp B | | Ex 2 vs Comp A | |
|---|---|---|---|---|---|---|
| Attribute | Ex 1 | Comp A | Ex 1 | Comp B | Ex 2 | Comp A |
| Lather Creaminess | 15 | 20 | — | — | 7* | 29* |
| Slippery feel of hair - wet | 30* | 6* | 19 | 17 | 28* | 8* |
| Ease of wet combing | 14 | 17 | 17 | 15 | 19 | 13 |
| Gloss of dry hair | 27* | 8* | 12 | 20 | 23^ | 11^ |
| Body of dry hair | 21 | 14 | 17 | 18 | 16 | 18 |
| Hold of dry hair | 14 | 16 | 22+ | 10+ | 12 | 18 |
| Ease of dry comb | 12+ | 23+ | 12 | 18 | 13 | 18 |
| Lack of flyaway | 21* | 4* | 8 | 5 | 21* | 4* |
| Softness dry | 16 | 20 | 15 | 19 | 22+ | 10+ |
| Clean feel (panellist) | 11 | 14 | 10 | 16 | 15 | 10 |

*significant at 1%
+significant at 5%
^significant at 10%

Foam Testing

The formulations shown in the following Table were evaluated for foam height using the Ross Miles test as follows:

The measurements were taken at room temperature. A solution of 1 part test formulation to 9 parts water was prepared, any foam on the surface of the liquid was removed. 200 ml of liquor was placed in both the upper and lower chambers. The liquid was allowed to run from the upper chamber hitting the centre of the surface of the liquid in the lower chamber. 5 minutes after all the liquid had run through the foam height at four points around the chamber was recorded (and the average taken). The equipment was cleaned and the measurement repeated a further two times for each of the test solutions. An average of all three values was taken.

The results of the testing are shown at the foot of the Table.

| Ingredient % active | Ex 1 | Ex 2 | Comp Ex A | Comp Ex B (i) | Comp Ex B (ii) | Ex 3 | Ex 4 | Ex 5 | Ex 6 |
|---|---|---|---|---|---|---|---|---|---|
| CTAC | 2 | 2 | | | 1 | 2 | 2 | 2 | 2 |
| Behenyl alcohol | 9.8 | 9.8 | | | | 9.8 | 9.8 | 9.8 | 9.8 |
| Natrosol HHXR | 0.8 | 0.5 | | | | 0.8 | 0.8 | 0.8 | 0.8 |
| Montaline C40 | 10 | 10 | | | | 10 | | | |
| Silicone DC2 1310 | | 0.5 | | | | 0.5 | 0.5 | 0.5 | 0.5 |
| SLES | | | 14 | 14 | | | | | |
| CAPB | | | 2 | 2 | | | | | |
| Carbopol 980 | | | 0.4 | | | | | | |
| EGDS | | | 1.5 | 1.5 | | | | | |
| Silicone X2 1766 | | | 1.5 | | | | | | |
| Cetearyl Alcohol | | | | | 3 | | | | |
| Sodium luaroamphoacetate | | | | | 2 | | | | |
| Berol 556 | | | | | | | 10 | | |
| Ethoquad C12 | | | | | | | | 10 | |
| HOE S3996 | | | | | | | | | 10 |
| Ross Miles Lather height (cm) | 11.1 | 11.2 | 13.4 | 14.0 | 1.3 | 11.6 | 8.7 | 10.6 | 10.9 |

What is claimed is:

1. A hair treatment composition having cleansing and conditioning properties comprising, in an aqueous medium:
   (i) a first cationic surfactant corresponding to the general formula (I):

$[N(R_1)(R_2)(R_3)(R_4)]^+(X)^-$ in which $R_1$ is a hydrocarbyl chain having 16 or more carbon atoms, and $R_2$, $R_3$ and $R_4$ are independently selected from hydrocarbyl chains of from 1 to about 30 carbon atoms, X is a salt-forming anion selected from the group consisting of halogen, acetate, citrate, lactate, glycolate, phosphate, nitrate, sulphate, and alkylsulphate radicals;
   (ii) a second cationic surfactant corresponding to the general formula (II) or the general formula (III); general formula (II) being:

$[N(R_1)(R_2)(R_3)(R_4)]^{3O}(X)^-$ in which $R_1$ is a hydrocarbyl chain having from 8 to 14 carbon atoms, and $R_2$, $R_3$ and $R_4$ are independently selected from (a) hydrocarbyl chains of from 1 to about 30 carbon atoms, or (b) functionalised hydrocarbyl chains having from 1 to about 30 carbon atoms and containing one or more aromatic, ether, ester, amido or amino moieties present as substituents or as linkages in the radical chain, X is a salt-forming anion selected from the group consisting of halogen, acetate, citrate, lactate, glycolate, phosphate, nitrate, sulphate, and alkylsulphate radicals, and at least one of the $R_1$ to $R_4$ radicals contains one or more hydrophilic moieties selected from the group consisting of alkoxy, polyoxyalkylene, alkylamido, hyidroxyalkyl, alkylester, and combinations thereof, and general formula (III) being:

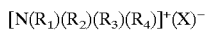

in which
$R_1$ is a linear or branched, saturated or unsaturated hydrocarbyl chain having from 5 to 30 carbon atoms, which is linked either directly to the quaternary nitrogen atom or via a functionalised link moiety selected from the group consisting of an alkylester, alkylamido, alkoxy, and combinations thereof;

$R_2$ is a linear or branched, saturated or unsaturated hydrocarbyl chain having from 1 to 30 carbon atoms, and is optionally substituted with one or more hydroxy groups;

$R_3$ is a linear or branched, saturated or unsaturated hydrocarbyl chain having from 1 to 30 carbon atoms, and optionally contains one or more groups selected from the group consisting of hydroxy, alkoxy, polyoxyalkylene groups, and combinations thereof, present as either substituents on the hydrocarbyl chain or as linkages in the hydrocarbyl chain;

$R_4$ is a linear or branched saturated or unsaturated hydrocarbyl chain having from 1 to 30 carbon atoms, and which contains one or more groups selected from the group consisting of hydroxy, aromatic, ether, ester, amido, amino groups, and combinations thereof, present as either substituents on the hydrocarbyl chain or as linkages in the hydrocarbyl chain; and, X is a salt-forming anionic selected from the group consisting of halogen, acetate, citrate, lactate, glycolate, phosphate, nitrate, sulphate, and alkylsulphate radicals;

and wherein the first cationic surfactant (i) and second cationic surfactant (ii) together amount to more than 10% by weight of the hair treatment composition and wherein said hair treating composition further comprises a 12 to 22 carbon chain fatty alcohol present in a weight ratio relative to cationic surfactant (i) from 10:1 to 1:10 for maintaining good cosmetic in-use and rheologic characteristics.

2. A hair treatment composition according to claim 1, in which, in general formula (III),
$R_1$ is a hydrocarbyl chain having from 8 to 20 carbon atoms, and, if present, the functionalised link moiety linking the hydrocarbyl chain to the quaternary nitrogen atom is a $C_1$–$C_3$ alkylester, a $C_1$–$C_3$ alkylamido or a $C_1$–$C_3$ alkoxy, $R_2$ and $R_3$ are independently hydrocarbyl chains having from 1 to 20 carbon atoms;

$R_4$ is a hydrocarbyl chain having from 1 to 20 carbon atoms.

3. A hair treatment composition according to claim 2, in which any alkoxy or polyoxyalkylene substituent or linkage groups present in $R_3$ and/or $R_4$ are $C_1$–$C_3$ groups.

4. A hair treatment composition according to claim 1, in which the cationic surfactant (ii) corresponds to the general formula (IV):

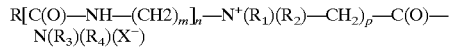

in which

R is a linear or branched alkyl or alkenyl radical having from 5 to 30 carbon atoms;

m is an integer equal to 2 or 3;

n is an integer equal to 0 or 1;

$R_1$ and $R_2$ are independently:
an alkyl radical having from 1 to 4 carbon atoms, or a hydroxymethyl, hydroxyethyl or hydroxypropyl radical;

p is an integer from 1 to 3;

$R_3$ is a group: $-(CH_2)_q-(O)_y-(CH_2-CH(R_5)-O)_r-H$ in which:
q is an integer from 1 to 5,
y is an integer equal to 0 or 1,
$R_5$ is a hydrogen atom or a methyl radical, and
r is an integer from 0 to 10, it being specified that r and y cannot simultaneously be equal to 0;

or a group: $-(CH_2)_s-(CHOH)_t-(CH_2)_u-CH_3$
in which:
s is an integer from 0 to 2,
t is an integer from 0 to 6, and
u is an integer from 0 to 5;

or a group: $-(CH_2)_v-(CHOH)_w-CH_2OH$
in which:
v is an integer equal to 0 or 1, and
w is an integer from 1 to 6;

$R_4$ is a hydrogen atom or has the same meaning as $R_3$; and

X is a water-soluble salt forming anion.

5. A hair treatment composition according to claim 4, in which in general formula (IV) R is a linear or branched alkyl or alkenyl radical having from 8 to 18 carbon atoms, m is equal to 3, n is equal to 1, $R_1$ and $R_2$ are methyl radicals, $R_3$ is a 2-hydroxyethyl radical and $R_4$ is a hydrogen atom.

6. A hair treatment composition according to claim 1, in which the cationic surfactant (ii) corresponds to the general formula (V):

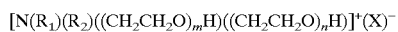

in which:
$R_1$ is linear or branched alkyl or alkenyl radical having from 5 to 30 carbon atoms;
$R_2$ is a $C_1$–$C_3$ alkyl group; and
m and n are each independently integers from 1 to 15; and
X is a salt-forming anion selected from the group consisting of halogen, acetate, citrate, lactate, glycolate, phosphate, nitrate, sulphate, and alkylsulphate radicals.

7. A hair treatment composition according to claim 1, in which the cationic surfactant (ii) corresponds to the general formula (VI):

in which:

R$_1$ is a linear or branched alkyl or alkenyl radical having from 5 to 30 carbon atoms;

R$_2$ and R$_3$ are independently selected from C$_1$–C$_3$ alkyl groups, and m is an integer from 1 to 15; and X is a salt-forming anion selected from the group consisting of halogen, acetate, citrate, lactate, glycolate, phosphate, nitrate, sulphate, and alkylsulphate radicals.

8. A composition according to claim 1, which has a foam height of more than 20 mm, when measured by the Ross-Miles test.

9. A composition according to claim 1, in which the cationic surfactant (i) is selected from cetyl trimethyl ammonium chloride, stearyl trimethyl ammonium chloride, behenyl trimethyl ammonium chloride, and mixtures thereof.

10. A composition according to claim 1 which is in the form of a rinse-off conditioner, a leave-on conditioner or a conditioning mousse.

11. A hair treatment composition according to claim 1, which further comprises a surfactant selected from the group consisting of an anionic surfactant, an amphoteric surfactant or a mixture thereof, wherein said surfactant is no more than 3% by weight based on total weight of the composition.

12. A hair treatment composition having cleaning and conditioning properties comprising, in an aqueous medium:

(i) a first cationic surfactant corresponding to the general formula (I):

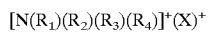

in which R$_1$ is a hydrocarbyl chain having from 10 or more carbon atoms, and R$_2$, R$_3$ and R$_4$ are independently selected from hydrocarbyl chains of from 1 to about 30 carbon atoms, X is a salt-forming anion selected from the group consisting of halogen, acetate, citrate, lactate, glycolate, phosphate, nitrate, sulphate, and alkylsulphate radicals, and the total sum of the number of carbon atoms in R$_1$, R$_2$, R$_3$ and R$_4$ is 22 or greater;

(ii) a second cationic surfactant corresponding to the general formula (II) or the general formula (III);

general formula (II) being:

in which R$_1$ is a hydrocarbyl chain having from 8 to 14 carbon atoms, and R$_2$, R$_3$ and R$_4$ are independently selected from (a) hydrocarbyl chains of from 1 to about 30 carbon atoms, or (b) functionalised hydrocarbyl chains having from 1 to about 30 carbon atoms and containing one or more aromatic, ether, ester, amido or amino moieties present as substituents or as linkages in the radical chain, X is a salt-forming anion selected from the group consisting of halogen, acetate, citrate, lactate, glycolate, phosphate, nitrate, sulphate, and alkylsulphate radicals, and at least one of the R$_1$ to R$_4$ radicals contains one or more hydrophilic moieties selected from the group consisting of alkoxy, polyoxyalkylene, alkylamido, hydroxyalkyl, alkylester, and combinations thereof, and general formula (III) being:

in which

R$_1$ is a linear or branched, saturated or unsaturated hydrocarbyl chain having from 5 to 30 carbon atoms, which is linked either directly to the quaternary nitrogen atom or via a functionalised link moiety such as an alkylester, alkylamido or an alkoxy, or combinations thereof;

R$_2$ is a linear or branched, saturated or unsaturated hydrocarbyl chain having from 1 to 30 carbon atoms, and is optionally substituted with one or more hydroxy groups;

R$_3$ is a linear or branched, saturated or unsaturated hydrocarbyl chain having from 1 to 30 carbon atoms, and optionally contains one or more groups selected from the group consisting of hydroxy, alkoxy and polyoxyalkylene groups, and combinations thereof, present as either substituents on the hydrocarbyl chain or as linkages in the hydrocarbyl chain;

R$_4$ is a linear or branched saturated or unsaturated hydrocarbyl chain having from 1 to 30 carbon atoms, and which contains one or more groups selected from the group consisting of hydroxy, aromatic, ether, ester, amido and amino groups, and combinations thereof, present as either substituents on the hydrocarbyl chain or as linkages in the hydrocarbyl chain; and, X is a salt-forming anionic selected from the group consisting of halogen, acetate, citrate, lactate, glycolate, phosphate, nitrate, sulphate, and alkylsulphate radicals;

and wherein the first cationic surfactant (i) and second cationic surfactant (ii) together amount to more than 2% by weight of the hair treatment composition;

and wherein said hair treatment composition further comprises a 12 to 22 carbon chain fatty alcohol present in a weight ratio relative to cationic surfactant (i) from 10:1 to 1:10 for maintaining good cosmetic in-use and rheologic characteristics.

* * * * *

UNITED STATES PATENT AND TRADEMARK OFFICE
CERTIFICATE OF CORRECTION

PATENT NO. : 6,645,480 B2
DATED : November 11, 2003
INVENTOR(S) : Colin Christopher Giles It is certified that error appears in the above-identified patent and that said Letters Patent is hereby corrected as shown below:

Column 10,
Line 67, "$[N(R_1)(R_2)(R_3)(R_4)]^{30}(X)^-$" should read -- $[N(R_1)(R_2)(R_3)(R_4)]^+(X)^-$ --

Column 14,
Line 12, "$[N(R_1)(R_2)(R_3)(R_4)]^+(X)^+$" should read -- $[N(R_1)(R_2)(R_3)(R_4)]^+(X)^-$ --

Signed and Sealed this

Twenty-third Day of March, 2004

JON W. DUDAS
*Acting Director of the United States Patent and Trademark Office*